(12) United States Patent
Delagrave et al.

(10) Patent No.: US 8,877,492 B2
(45) Date of Patent: Nov. 4, 2014

(54) COMPOSITIONS AND METHODS FOR THE PRODUCTION OF ALPHA-HERPESVIRUSES

(75) Inventors: Simon Delagrave, Stoneham, MA (US); Rachid Oubelaid, Vitry-sur-Seine (FR); John Hamberger, Milford, NJ (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 274 days.

(21) Appl. No.: 13/057,788

(22) PCT Filed: Aug. 11, 2009

(86) PCT No.: PCT/US2009/053407
§ 371 (c)(1),
(2), (4) Date: Apr. 28, 2011

(87) PCT Pub. No.: WO2010/019572
PCT Pub. Date: Feb. 18, 2010

(65) Prior Publication Data
US 2011/0201087 A1    Aug. 18, 2011

Related U.S. Application Data

(60) Provisional application No. 61/188,552, filed on Aug. 11, 2008.

(51) Int. Cl.
*C12N 15/86* (2006.01)
*C12N 5/00* (2006.01)
*C12N 7/00* (2006.01)
*C12N 15/63* (2006.01)

(52) U.S. Cl.
CPC .............. *C12N 7/00* (2013.01); *C12N 2500/76* (2013.01); *C12N 5/0018* (2013.01); *C12N 2710/16052* (2013.01); *C12N 2500/36* (2013.01); *C12N 2500/34* (2013.01); *C12N 2710/16051* (2013.01)
USPC ......................................... 435/325; 424/93.1

(58) Field of Classification Search
None
See application file for complete search history.

(56) References Cited

U.S. PATENT DOCUMENTS

| | | | |
|---|---|---|---|
| 5,360,736 A * | 11/1994 | Provost et al. .............. 435/235.1 |
| 5,607,852 A | 3/1997 | Provost et al. |
| 6,267,967 B1 * | 7/2001 | Johnston et al. ........... 424/229.1 |
| 2006/0141566 A1 | 6/2006 | Calton et al. |
| 2006/0286668 A1 | 12/2006 | Price et al. |
| 2007/0219159 A1 | 9/2007 | Wallace et al. |

FOREIGN PATENT DOCUMENTS

| EP | 0 573 107 A2 | 12/1993 |
|---|---|---|
| WO | WO 2007/016239 A2 | 2/2007 |

OTHER PUBLICATIONS

Dudek et al. Virology, Public available on line on Nov. 19, 2027, vol. 371, pp. 165-175.*
Costa et al. J. Virology, 2000, vol. 74, pp. 7963-7971.*
International Preliminary Report on Patentability for International Application No. PCT/US2009/053407, dated Feb. 15, 2011.
Extended European Search Report from European Patent Application No. 09807164.0, dated Dec. 19, 2011 (date of completion of search) and Dec. 27, 2011 (date of mailing of report).
"Immunization with Herpes Simplex Virus Type 2 Replication-Defective Mutant, d15-29, Reduces Latent Viral DNA in Mouse Trigeminal Ganglia," Vaccine Weekly, Abstract. <http://www.highbeam.com/doc/1G1-53934235.html>, Feb. 22, 1999.
International Search Report from International Application No. PCT/US2009/053407, dated Sep. 18, 2009 (date of completion of search) and Sep. 28, 2009 (date of mailing of report).
Written Opinion from International Application No. PCT/US2009/053407, dated Sep. 18, 2009 (date of completion of opinion) and Sep. 28, 2009 (date of mailing of opinion).

* cited by examiner

*Primary Examiner* — Bao Li
(74) *Attorney, Agent, or Firm* — Clark & Elbing LLP

(57) ABSTRACT

The present invention relates to virus growth media that improve the yield of alpha-herpesviruses (e.g., HSV-2) grown in cell cultures. The growth media of the invention include two additives, a disaccharide and a lipid mixture, that can be added to serum-free or serum-enriched growth media to improve the efficiency of virus production. The invention further provides methods of producing alpha-herpesviruses (e.g., HSV-2) in such growth media.

19 Claims, 8 Drawing Sheets

COMPOSITIONS AND METHODS FOR THE PRODUCTION OF ALPHA-HERPESVIRUSES

CROSS-REFERENCE TO RELATED APPLICATIONS

This application is the U.S. national stage filing under 35 U.S.C. §371 of international application PCT/US2009/053407, filed Aug. 11, 2009, which claims benefit of U.S. Provisional Application No. 61/188,552, filed Aug. 11, 2008.

FIELD OF THE INVENTION

The invention provides compositions including growth media that improve the yield of alpha-herpesviruses (e.g., HSV-2) grown in cell cultures. The growth media of the invention include at least two additives, a disaccharide and a lipid mixture, which can be added to serum-free or serum-enriched growth media to improve the efficiency of virus production. The invention further provides methods of producing alpha-herpesviruses (e.g., HSV-2) in such growth media.

BACKGROUND OF THE INVENTION

The alpha-herpesvirus herpes simplex virus type 2 (HSV-2) is the cause of genital herpes, which can be treated symptomatically but not cured. Hallmarks of herpes virus infection include the establishment of lifelong, latent infections that can reactivate to cause one or more rounds of disease, as well as transmission in the absence of symptoms. Transmission of HSV-2 to newborns at the time of delivery may lead to devastating systemic infection with encephalitis. Further, immunocompromised individuals are at increased risk of serious disseminated infection. Also, HSV-2 has been shown to increase significantly the risk of becoming infected with HIV-1, the virus that causes AIDS. The development of vaccines to prevent or treat HSV-2 infection is therefore of considerable importance.

The manufacture of virus-based vaccines (e.g., attenuated or inactivated virus particles) generally involves the infection of mammalian cell lines in vitro with a small quantity of a virus, followed later by harvest of large quantities of progeny virus. The mammalian cells are propagated in growth media, which are complex solutions containing a large number of different salts, small organic molecules such as carbohydrates and lipids, and macromolecules such as peptides and proteins. Optimization of virus production methods is important to the development of efficiently produced, cost-effective herpes virus vaccines.

SUMMARY OF THE INVENTION

In a first aspect, the invention provides compositions useful for growing cells in culture (e.g., monolayer culture). The compositions of the invention include growth media including between 5 mM and 500 mM (e.g., about 50 mM and about 80 mM, or between about 50 mM and about 80 mM) of a disaccharide (e.g., sucrose), and a lipid mixture (e.g., a lipid mixture derived from a plant or that is synthetically produced, and/or including cholesterol or stigmastanol). The cells grown in the compositions of the invention can be, for example, Vero, MRC-5, BHK, CEM, and LL-1 cells. The disaccharide can be, for example, sucrose, lactose, maltose, trehalose, or cellobiose, or a mixture thereof. In an example, the compositions also contain methyl-β-cyclodextrin or serum, such as fetal bovine serum (FBS). The compositions of the invention can, for example, increase production of a virus in cells by at least 10%, relative to cells grown in compositions lacking the disaccharide and lipid mixture. The virus grown in the media can be an alpha-herpesvirus, such as herpes simplex virus 1 (HSV-1) or herpes simplex virus 2 (HSV-2). In one example, the HSV-2 has one or more inactivating mutations (e.g., deletions) in $U_L5$ and $U_L29$ (e.g., virus dl5-29), optionally in combination with one or more inactivating mutations (e.g., deletions) in $U_L41$ (e.g., virus dl5-29-41). Further, the compositions of the invention can include, in addition to media components, as described herein, cells and/or viruses, as described herein.

In a second aspect, the invention provides methods of increasing virus production in cells, involving culturing the cells in a serum-free medium containing between 5 mM and 500 mM (e.g., about 50 mM or about 80 mM, or between about 50 mM and about 80 mM) of a disaccharide (e.g., sucrose), and a lipid mixture (e.g., a lipid mixture derived from a plant or that is synthetically produced, and/or including cholesterol or stigmastanol), where the medium increases production of a virus in cells by at least 10% relative to cells grown in a medium lacking the disaccharide and lipid mixture. In various examples, the cells are mammalian cells, such as Vero, MRC-5, BHK, CEM, or LL-1 cells. In another example, the cells (e.g., AV529-19 cells) can support the growth of a replication defective herpesvirus, such as dl5-29, by expression of herpesvirus polypeptides $U_L5$ and/or $U_L29$. The disaccharide can be, for example, sucrose, lactose, maltose, trehalose, or cellobiose, or a mixture thereof. In a further example, the medium contains methyl-β-cyclodextrin or serum, such as fetal bovine serum (FBS). The media used in the methods of the invention can, for example, increase production of a virus in cells by at least 10% relative to cells grown in a medium lacking a disaccharide and lipid mixture. The virus grown in the medium can be an alpha-herpesvirus, such as herpes simplex virus 1 (HSV-1) and herpes simplex virus 2 (HSV-2). In one example, the HSV-2 has one or more inactivating mutations (e.g., deletions) in $U_L5$ and $U_L29$ (e.g., virus dl5-29), optionally in combination with one or more inactivating mutations (e.g., deletions) in $U_L41$ (e.g., virus dl5-29-41).

The invention provides several advantages. In particular, the compositions of the invention improve the yield of herpes viruses grown in cell cultures, which provides benefits with respect to efficiency and cost of virus production methods.

Other features and advantages of the invention will be apparent from the following detailed description, the drawings, and the claims.

BRIEF DESCRIPTION OF THE DRAWINGS

FIG. 1 is a graph showing the average population doubling times of Vero cells (strain AV529-19) grown in three different cell culture media (OptiPro SFM, ExCell, and VP SFM AGT), with and without the addition of sucrose and a lipid mixture.

FIG. 2 is a graph showing the yield of HSV-2 virus dl5-29 (starting MOI=0.1) produced in AV529-19 cells grown in three different cell culture media (OptiPro SFM, ExCell, and VP SFM AGT), with and without the addition of sucrose and a lipid mixture.

FIG. 3 is a graph showing the total yield per flask of HSV-2 virus dl5-29 (starting MOI=0.1) produced in AV529-19 cells grown in three different cell culture media (OptiPro SFM, ExCell, and VP SFM AGT), with and without the addition of sucrose and a lipid mixture.

FIG. 4 is a graph showing the optimization of culture media additives in OptiPro SFM with 1% FBS. The horizontal line at ~13 pfu/cell indicates dl5-29 yield in OptiPro SFM (no FBS) with 1× each of sucrose and a lipid mixture. The horizontal line at ~8.5 pfu/cell indicates OptiPro SFM (no FBS) with no sucrose/lipid mixture additives.

Figure 7A:
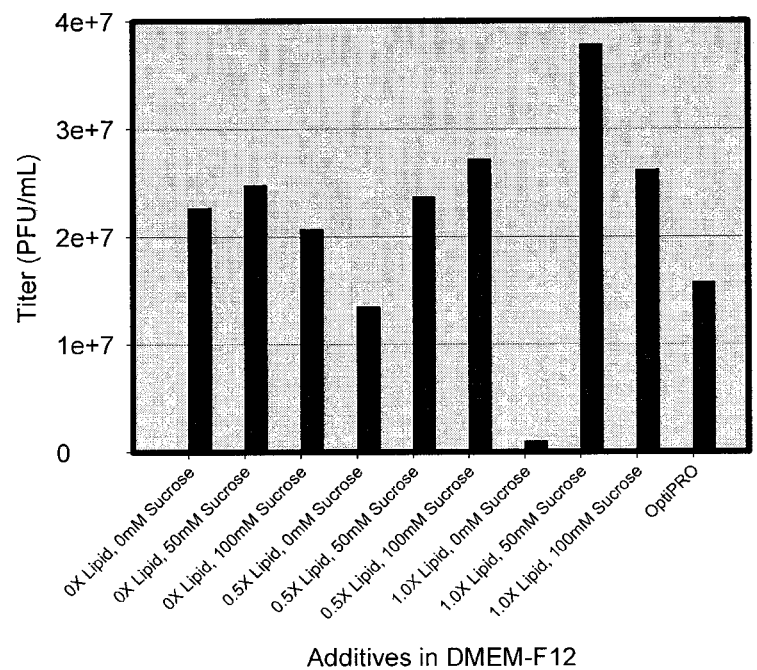
FIG. 7A is a graph showing viral titer resulting from incubation with the indicated amounts of sucrose and a lipid mixture in DMEM-F12.
Figure 7B:
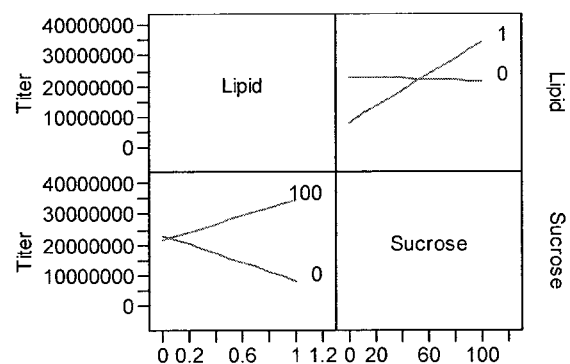

FIG. 7B is a graph showing the interaction profiles of optimum amounts of lipid concentrate and sucrose. The upper right quadrant shows titer as a function of sucrose concentration in the presence and absence of 1× lipid. The lower left quadrant shows titer as a function of lipid concentration in the presence and absence of 100 mM sucrose.

Figure 8:
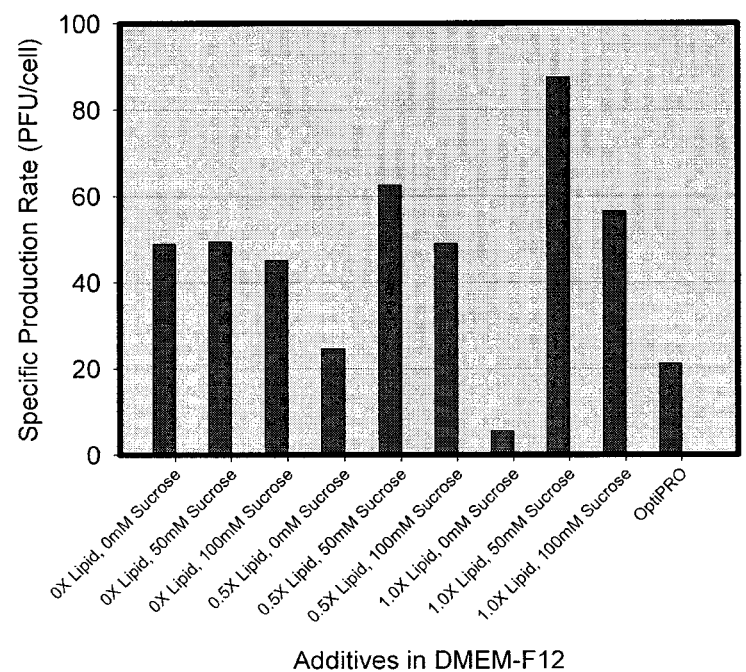

FIG. 8 is a graph showing PFU/cell production of cells incubated with the indicated amounts of sucrose and a lipid mixture in OptiPro.

DETAILED DESCRIPTION OF THE INVENTION

The invention provides compositions and methods for use in virus production. The compositions of the invention include a cell culture medium supplemented with disaccharide and lipid mixture additives. The compositions can be used to culture cells infected with alpha-herpesviruses and, advantageously, result in high viral yields of such cultures. As discussed further below, in one example, the compositions and methods of the invention are used in the production of a herpes simplex virus, which can be used, e.g., as a vaccine or as a delivery vector. The compositions and methods of the invention are described in further detail as follows.

The present invention is based on the discovery that the addition of a disaccharide, sucrose, and a lipid mixture to a base cell culture medium increases the yield of an alpha-herpesvirus (i.e., HSV-2 strain dl5-29; see below) by over 100% in static cultures. The viral growth media can be formulated with or without fetal bovine serum (FBS). This result is applicable to other growth media, including VP-SFM-AGT (Invitrogen/GIBCO) and ExCell (SAFC)(also see below). The effect of the two additives is due to increased productivity of virus on a per-cell basis, and not due to increased cell density per growth vessel. A matrix analysis of several additive concentrations was performed to ensure that optimal concentrations of both additives were identified. The invention was first demonstrated in small culture flasks and later extended to large 10-layer Nunc cell factories (NCFs). The compositions and methods of the invention can also be used in bioreactors for large-scale virus production (e.g., for commercial viral vaccine production).

As discussed further below, the compositions and methods of the invention can be used to increase the production efficiency of alpha-herpesviruses (e.g., HSV-2), such as replication-defective strains that can be used in therapeutic or prophylactic vaccines or as delivery vectors.

Viral Growth Media

Figure 1:
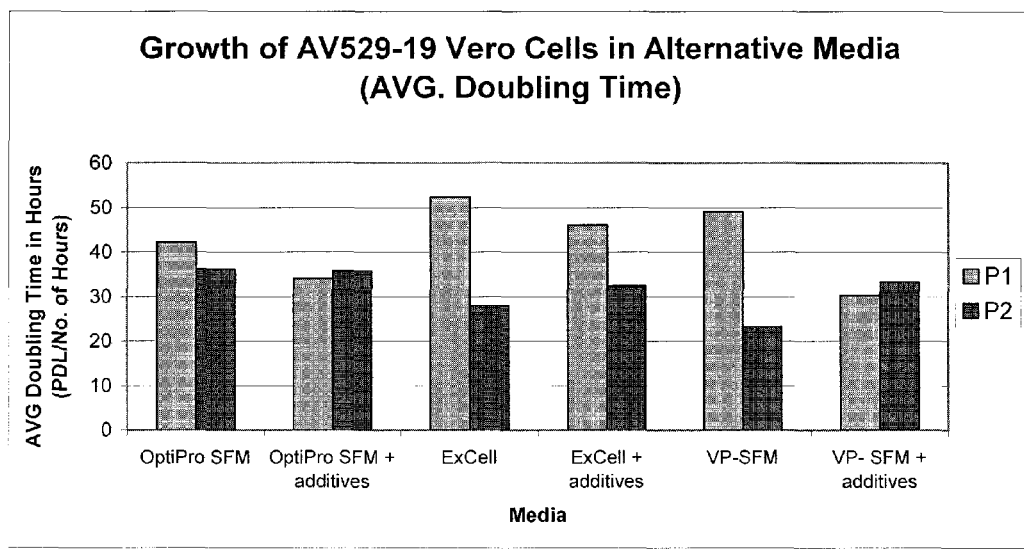
Figure 2:
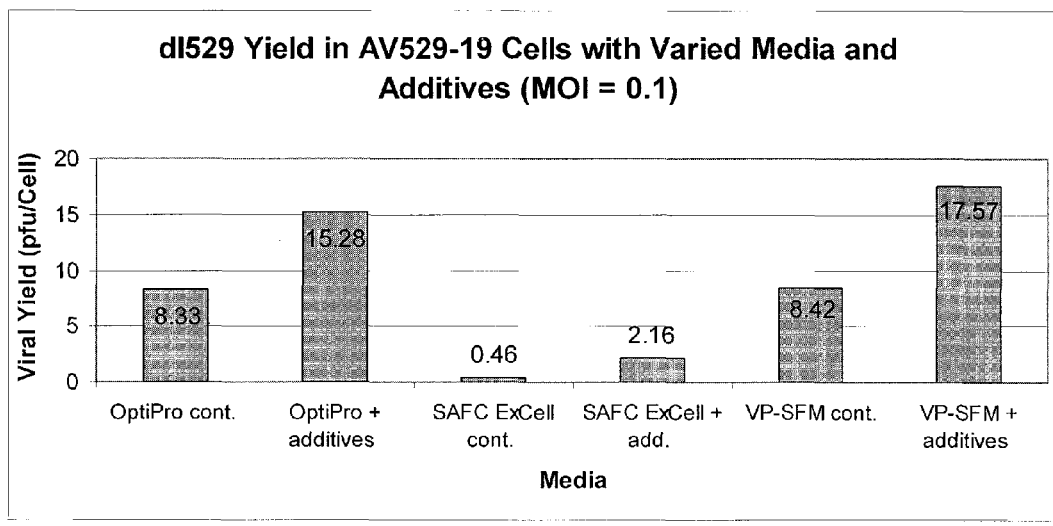
Figure 3:
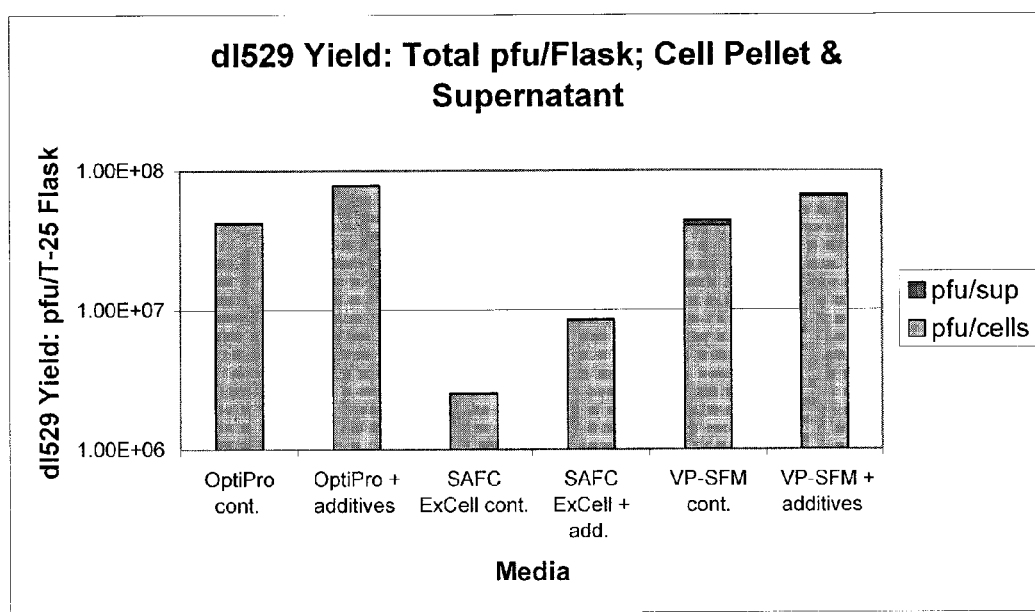

The invention provides growth media that contain both a disaccharide (e.g., sucrose) and a lipid mixture that, when used to produce an alpha-herpesvirus (e.g., HSV-2), is capable of increasing the viral yield. The disaccharide and lipid mixture can be added to a base cell culture medium suitable for the culture of cells supporting virus growth, such as Vero, BHK, and MRC-5 cells. Exemplary base culture media include OptiPro SFM (Invitrogen/GIBCO), ExCell (SAFC), VP SFM AGT (Invitrogen/GIBCO) (FIGS. 1-3), MegaVir (HyClone), DMEM-F12 (Sigma Aldrich), and any other medium in which the cells and virus can grow, as can be tested using standard methods (see, e.g., below). A cell culture medium can be formulated with additional nutrient rich additives (e.g., with serum, such as fetal bovine serum) or without such additives (e.g., a "serum-free" medium such as OptiPro SFM). Exemplary formulations of growth media of the invention are described below.

Disaccharides

Disaccharides for use in the compositions and methods of the invention include, for example, sucrose, lactose, maltose, trehalose, and cellobiose. The disaccharides (e.g., sucrose) can be added to a suitable growth medium at a concentration of, e.g., 1 mM, 5 mM, 10 mM, 20 mM, 30 mM, 40 mM, 50 mM, 60 mM, 70 mM, 80 mM, 90 mM, 100 mM, 200 mM, 300 mM, 400 mM, 500 mM, or more (or at any amount in ranges between any of the amounts listed above; when ranges are provided herein, they include both ends of the ranges, as well as all amounts between the ends, unless otherwise indicated). Thus, in specific examples, the amount of disaccharide (e.g., sucrose) can be 50 mM, about 50 mM, 80 mM, about 50 mM, or between 50 mM and 80 mM. An exemplary method of determining optimal concentrations of a disaccharide for use with any given virus or cell line combination is described below. Mixtures of disaccharides can also be used in any of the compositions or methods of the invention.

Lipid Mixtures

Lipid mixtures used in the present invention can contain cholesterol, stigmastanol, other lipids, or combinations of lipids (including, e.g., cholesterol and/or stigmastanol). The lipid mixtures can be naturally or synthetically derived. Naturally derived lipids can be isolated from an animal (e.g., a mammal, such as a cow) or isolated from a plant (e.g., soybean). Lipid formulations derived from non-animal sources (e.g., synthetic lipids or lipids derived from plants) may be preferred in some instances for use in viral growth media for the production of an alpha-herpesvirus (e.g., HSV-2) for use in vivo (e.g., in the treatment of human patients).

A method of determining effective and suitable concentrations of lipid mixtures for increasing the production of an alpha-herpesvirus HSV-2, strain dl5-29 is described herein (see, e.g., FIG. 4), and can be applied in the context of other viruses, such as those described herein. Prepared lipid mixtures for use in the compositions and methods of the invention are known in the art (e.g., Invitrogen/GIBCO 250× Cholesterol Lipid Mixture). Other lipid mixtures are described by Gorfien et al., Biotechnol. Prog. 16:682-687, 2000. Other examples of such mixtures that can be used in the invention include adult bovine serum (Sigma Chemical Co., e.g., Catalog No. L-4646), Ex-Cyte lipid I or Very Low Endotoxin (VLE) lipid (Miles Inc., Catalog No. 82-004-7, 82-004-8, and 82-019-1), and soybean lipid extract (Boehringer Mannheim Biochemicals; e.g., Catalog No. 1074-482; also see Iscove et al., J. Expt. Med. 147:923-933, 1979).

Alpha-Herpesviruses

Alpha-herpesviruses are a subfamily of the linear, double-stranded family of DNA viruses designated Herpesviridae. Alpha-herpesviruses include the genera Simplexvirus (e.g., ateline herpesvirus 1, bovine herpesvirus 2, cercopithecine herpesvirus 2, human herpesvirus 1 (herpes simplex virus-1; HSV-1), human herpesvirus 2 (herpes simplex virus-2; HSV-2), macacine herpesvirus 1 (previously known as cercopithecine herpesvirus 1), macropodid herpesvirus 1 and 2, papiine herpesvirus 2 (previously known as cercopithecine herpesvirus 16), and saimiriine herpesvirus 1), Varicellovirus (e.g., bovine herpesvirus 1, bovine herpesvirus 5, bubaline herpesvirus 1, canid herpesvirus 1, caprine herpesvirus 1, cercopithecine herpesvirus 9, cervid herpesvirus 1 and 2, equid herpesvirus 1, 3, 4, 6 (tentative), 8 and 9, felid herpesvirus 1, human herpesvirus 3 (varicella zoster virus, VZV), phocid herpesvirus 1, and suid herpesvirus 1), Mardivirus (e.g., columbid herpesvirus 1, gallid herpesvirus 2, gallid herpesvirus 3, and meleagrid herpesvirus 1), and Iltovirus (e.g., gallid herpesvirus 1, psittacid herpesvirus 1, chelonid herpesvirus 5, and chelonid herpesvirus 6).

A virus grown in the growth medium of the invention can be any alpha-herpesvirus, or any virus derived therefrom, for example, HSV-1 or HSV-2 strains. An alpha-herpesvirus produced according to the methods of the invention can have, for example, the sequence of an HSV-1 or HSV-2 genome modified by nucleotide mutations, including deletions and insertions, such as in the viruses described above and elsewhere herein. In particular, derivatives that can be used in the practice of the invention include viruses that have genetic mutations, particularly mutations that result in viral attenuation. Examples of such viruses include viruses having deletions in $U_L5$, $U_L29$, optionally in combination with $U_L41$, such as the HSV-2 strain dl5-29, which is described further below (see also WO 99/06069; U.S. Patent Publication No. 20020009462; DaCosta et al., J. Virology 74:7963-7971, 2000; and U.S. Pat. No. 6,841,373), as well as dl5-29-41 (see, e.g., WO 2007/016239).

Additional examples of mutant viruses that can be produced according to the methods of the invention include strain 1716 (MacLean et al., J. Gen. Virol. 72:631-639, 1991), strains R3616 and R4009 (Chou et al., Proc. Natl. Acad. Sci. USA 89:3266-3270, 1992), and R930 (Chou et al., J. Virol. 68(12):8304-8311, 1994), all of which have mutations in ICP34.5, strain dl20, which has a deletion in ICP4 (DeLuca et al., J. Virol. 56(2):558-570, 1985), strain d27-1 (Rice et al., J. Virol. 64(4):1704-1715, 1990), which has a deletion in ICP27, and strain d92, which has deletions in both ICP27 and ICP4 (Samaniego et al., J. Virol. 69(9):5705-5715, 1995). Replication competent viruses, such as those that contain one or more mutations in ICP10, and replication incompetent viruses, such as those that contain one or more mutations in the ICP8 gene, can also be produced according to the methods of the present invention.

In addition, viruses including nucleotide substitutions can also be used, for example, viruses containing 1, 2, 3, 4, 5, 6, 7, 8, 9, 10, 25, 50, 100, 200, 350, 500, or more nucleotide substitutions (as well as ranges including or between any of these values). The HSV-1 or HSV-2 genome can alternatively or additionally be modified by one or more insertions or by an extension at either or both ends. Viral derivatives that can be produced according to the methods of the invention also include intertypic recombinants containing DNA from, e.g., HSV-1 and HSV-2 strains. Derivatives typically have at least 70% sequence identity to a parent virus from which it is derived (e.g., HSV-1 or HSV-2), such as, for example, at least 80%, at least 90%, or at least 95% identity.

In addition to viruses used as vaccines against alpha-herpes virus infection, the methods of the invention can also be used to produce viruses that can be used in the delivery of heterologous, non-herpes virus sequences (see, e.g., WO 01/53507 and U.S. Pat. No. 7,118,755).

Herpes Simplex Virus 2 Strain dl5-29

Virus dl5-29 is a replication-defective HSV-2 virus, which contains deletions of the open reading frames for UL5, a component of the helicase-primase complex and an essential viral protein for viral DNA synthesis, and UL29, encoding the ICP8 DNA-binding protein, which is also an essential protein for viral DNA synthesis (see, e.g., WO 99/06069). Virus dl5-29 replicates only in cells engineered to complement the two genes, $U_L5$ and $U_L29$, which were deleted from its genome. The Vero cell line, a transformed cell line derived from African green monkey kidney cells, is often used as a cell substrate for the production of various vaccines. After genetic manipulation allows for expression of herpes viral genes $U_L5$ and $U_L29$, engineered Vero cell strain AV529-19 can be used as a substrate for the production of virus dl5-29. Use of the methods of the invention in the production of dl5-29 is described further below. Further, in addition to dl5-29, as described, for example, in WO 99/06069, the methods of the invention can be used in connection with other herpes viruses (e.g., HSV-2) having deletions in $U_L5$ and $U_L29$ open reading frames, or portions thereof, which render the viruses dependent upon complementation of these proteins for replication. In addition to dl5-29, as described above, the methods of the invention can be used in the production of viruses (e.g., dl5-29-41), which, in addition to having deletions in $U_L5$ and $U_L29$ sequences, also have an alteration (such as one or more deletions) of $U_L41$ nucleic acid sequences, by which the alteration increases the immunogenicity of the virus. A specific example of a virus having deletions in $U_L5$, $U_L29$, and $U_L41$ sequences (dl5-29-41), as well as general teachings of such viruses, are provided in WO 2007/016239.

Cell Lines

Cell lines used in the invention include cell lines that support alpha-herpesvirus growth, such as Vero (e.g., strain AV529-19), MRC-5, BHK, CEM, and LL-1 cells. A suitable cell line is one that hosts alpha-herpesviruses. Typically, the cell line is a mammalian cell line, such as a rodent, non-human primate (e.g., monkey), or human cell line. In order to allow growth of viruses lacking a gene encoding a protein essential for viral growth, the host cell line must include a nucleic acid sequence encoding the polypeptide missing from the virus (e.g., a deleted or mutated polypeptide). The host cell line can provide more than one polypeptide, in trans, to support viral growth (e.g., $U_L5$ and $U_L29$ are provided by AV529-19). Such polypeptides include structural and non-structural (e.g., functional) alpha-herpesvirus polypeptides, which can complement the growth of another virus in which the gene for the homologous polypeptide is deleted or otherwise mutated. The use of a Vero cell line to grow replication-incompetent herpesviruses is described in, e.g., U.S. Pat. No. 6,841,373, which is incorporated herein by reference.

Cell lines expressing functional herpes virus structural polypeptides can be produced by standard methods, such as by co-transfecting mammalian cells, for example, Vero, MRC-5, BHK, CEM, and LL-1 cells, with one or more vectors, such as a plasmid vector, including a nucleic acid molecule encoding the polypeptide(s), and a vector, such as a plasmid vector, encoding a selectable marker (e.g., the neo gene for neomycin/G418 antibiotic resistance). Clones possessing the selectable marker are then screened further to determine which clones also express functional polypeptide(s) using methods known to those skilled in the art (see, e.g., Rice et al., J. Virol. 64(4):1704-1715, 1990).

Compositions Including Media, Cells, and, Optionally, Viruses

The invention also includes compositions that include a medium of the invention, in combination with cells for use in virus production, according to the invention. These compositions can also, optionally, include viruses produced in the cells of the invention. Thus, compositions of the invention can contain media that includes a disaccharide (e.g., sucrose, lactose, maltose, trehalose, and cellobiose) at, for example, any of the concentrations noted above, as well as a lipid mixture (containing, for example, cholesterol and/or stigmastanol; and being synthetic or derived from animal or plant (e.g., soybean) sources). Specific examples of lipid mixtures and their amounts that can be included in such compositions are provided above. The media of the invention can include, for example, the base culture medias described above. Further, the media in the compositions of the invention can also optionally include components such as serum and/or amino acids, as described above.

Cells included in the compositions of the invention include those described above, e.g., Vero (e.g., AV529-19), MRC-5, BHK, CEM, and LL-1 cells, which may include transgenes encoding polypeptides that may be mutated or otherwise deficient in viruses produced in the cells. The cells can be plated, in suspension, intact, or in disrupted form (e.g., after sonication). Viruses included in the compositions of the invention include alpha-herpesviruses, including HSV-2 viruses as well as the other alpha-herpes viruses listed above. The viruses can include attenuating and/or other beneficial mutations as described herein, such as are present in viruses dl5-29 and dl5-29-41. The compositions of the invention can be used in methods for producing viruses as described herein.

Production of HSV-2 Strain dl5-29 Using Media Additives

The production of an HSV vaccine virus including deletions in $U_L5$ and $U_L29$ (e.g., dl5-29) can be performed using a complementary Vero cell line such as AV529-19, which is genetically engineered two express two genes, $U_L5$ and $U_L29$, that are necessary to support virus growth. Typically, viral yields have been below 10 pfu per cell, and methods were sought to attempt to boost the yield. The addition of sucrose and a lipid mixture to the growth and infection media improved yields to approximately 15 pfu per cell in preliminary studies using T-flasks and a limited number of NUNC Cell Factories (NCFs). Based upon these studies, optimized concentrations of sucrose and the lipid mixture were added to current media formulations on a larger scale and a production run utilizing four NCFs was performed to mimic a significant portion of a production run designed to produce viral seed or vaccine product for preclinical and clinical studies. The cells were seeded onto NUNC Cell Factories in OptiPro SFM media containing 10% Fetal Bovine Serum, 4 mM L-Glutamine, G418, and supplemented with 50 mM sucrose and 0.5× of a 250× concentrated lipid mixture (Invitrogen/GIBCO 250× cholesterol lipid concentrate) and grown for approximately 96 hours at 37° C. and 5% $CO_2$. Infection media consisted of the same OptiPro media, only with 1% FBS and without G418. Infections were at an estimated MOI of 0.01, and following approximately 72 hours incubation at 34° C. and 5% $CO_2$, NCFs were harvested. Aliquots were drawn from each unit for sonication and viral titer by standard plaque assay, and bulk harvests were centrifuged and pelleted in stabilization buffer for downstream processing. Plaque assay results indicated total viral yield for each NCF of about $2\times10^{10}$ pfu, with an average of 19 pfu/cell. This is more than a two-fold increase in viral yield compared to previous runs without the sucrose and cholesterol lipid concentrate additives. Viral yields between NCFs were consistent, ranging from 18 to 20 pfu/cell.

Identification of Optimal Media Additive Concentrations

Figure 4:
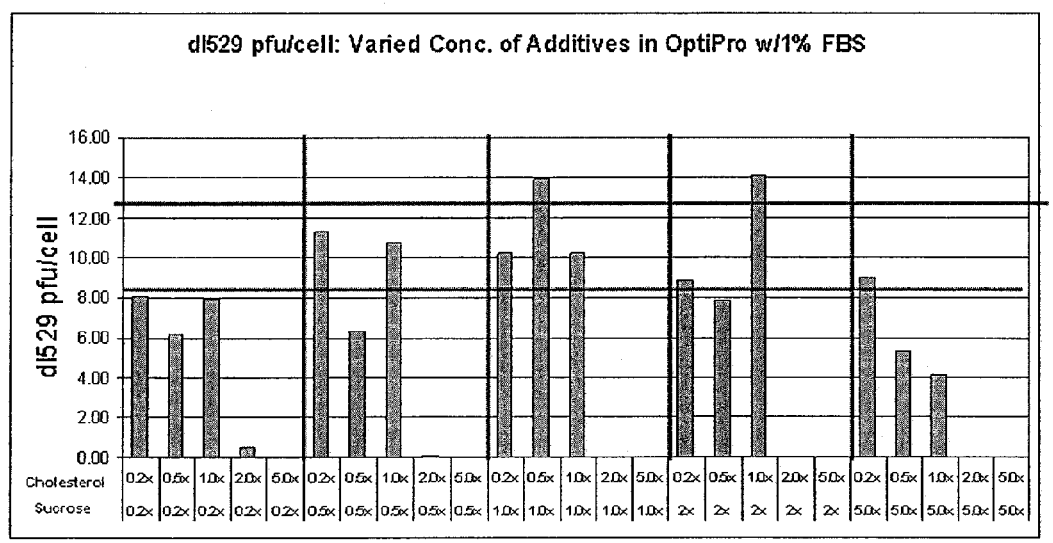
Figure 5A:
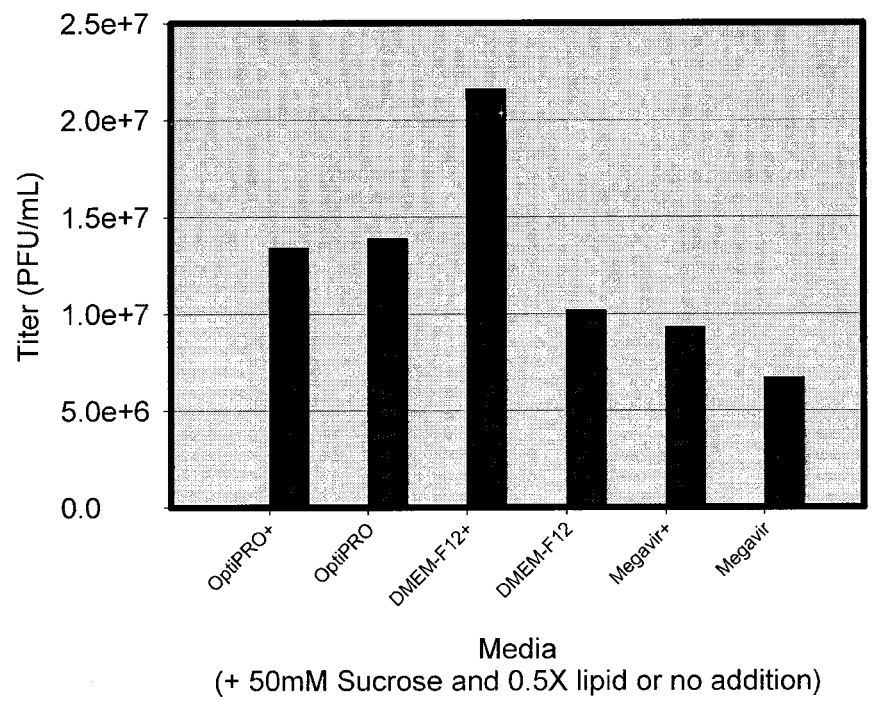
FIG. 5A is a graph showing virus titer from cells grown in three different culture media (OptiPro, DMEM-F12, and Megavir) in the presence or absence of sucrose and a lipid mixture.
Figure 5B:
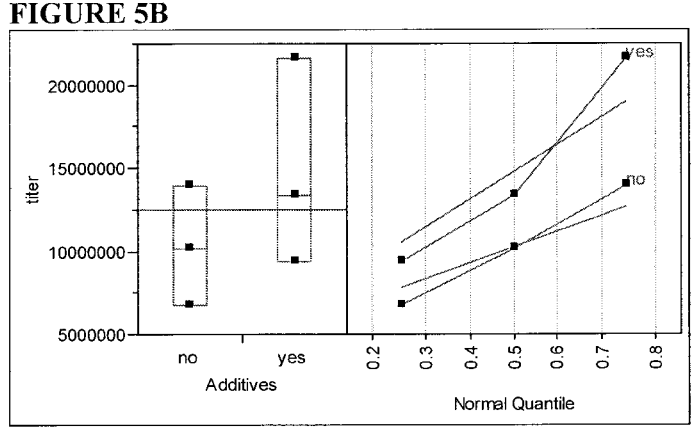
FIG. 5B is a oneway analysis of the data of FIG. 5A focused on the viral titer in the presence or absence of additives.
Figure 5C:
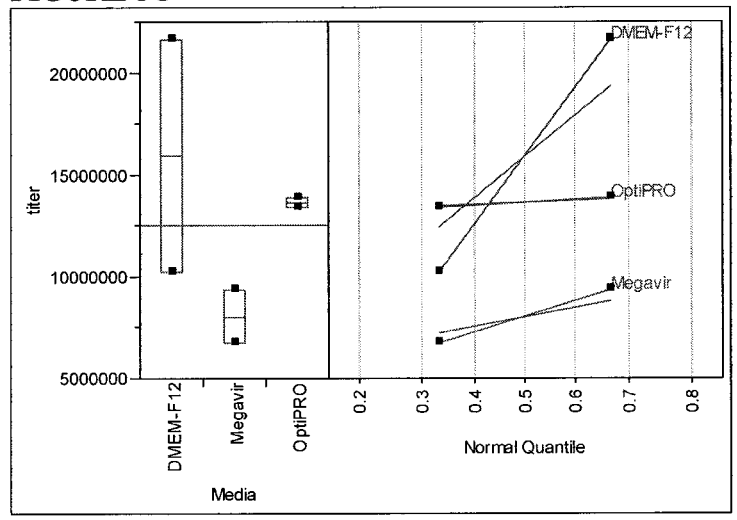
FIG. 5C is a oneway analysis of the data of FIG. 5A focused on the viral titer in cells incubated in the indicated basal media.
Figure 6:
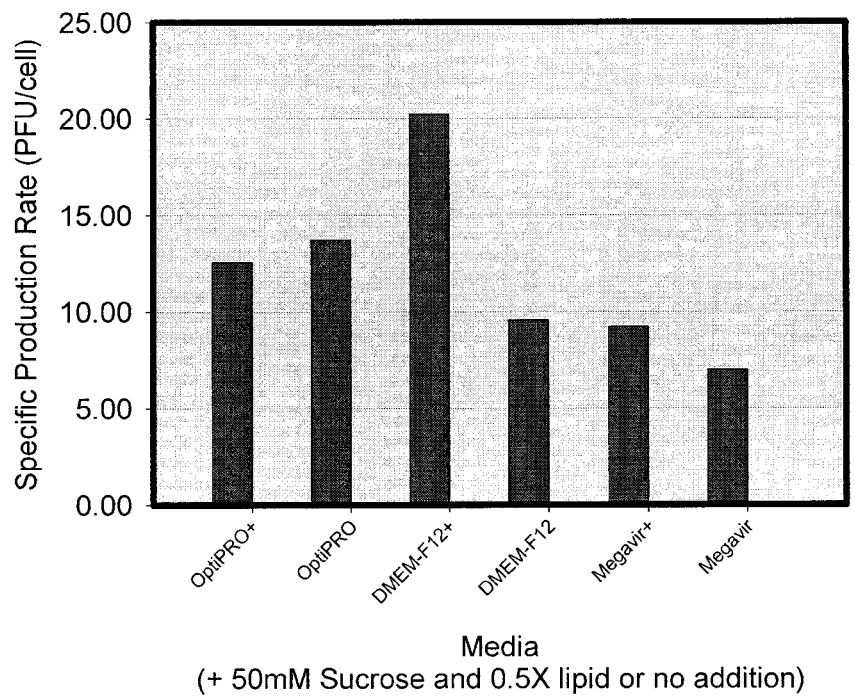
FIG. 6 is a graph showing the PFU/cell production of cells incubated in three different culture media (OptiPro, DMEM-F12, and Megavir) with and without sucrose and a lipid mixture.

Preliminary studies were performed in T-25 flasks to determine optimal concentrations of sucrose and a lipid mixture in growth and infection media during production of dl5-29 virus. This experiment to optimize additive concentrations consisted of a matrix of samples in concentrations of 0.2×, 0.5×, 1.0×, 2.0×, and 5.0× for each additive with 1× equivalent to 50 mM sucrose or 1× of a 250× cholesterol lipid concentrate. Raw data plaque counts were compiled onto an EXCEL spreadsheet, in which raw titers were calculated by multiplying the average plaque count by its dilution factor and dividing that quantity by 0.2. The resulting number was then multiplied by 5 to reflect the original 1/5 dilution of the sonicated sample to determine the pfu/mL. Standard deviations and % CV were also calculated to assist in determining the validity of the data. Data collected from this study are shown in FIG. 4, plotting calculated pfu/cell versus additive concentrations. All data shown are from growth and infection media containing serum, except the two horizontal lines at ~8.5 pfu/cell and 13 pfu/cell that indicate serum-free media without and with additives, respectively. The data indicate a substantial drop in titer with cholesterol concentration above 1×. The highest titers were achieved with 1× sucrose, 0.5× cholesterol and 2× sucrose, 1× cholesterol. Based upon these data, and for ease of formulation, the optimum concentrations used to go forward were sucrose at 1× (50 mM) and 0.5× of a 250× cholesterol lipid concentrate.

Confirmation of Additive Effect at Larger Scale

Based upon optimization study results, media for growth and infection were prepared for use in NCFs to compare the effects of these additives on a larger scale format. Two NCFs were prepared, one using media with additives (50 mM sucrose, 1× cholesterol lipid concentrate), the other without as a control. Results of this study are shown in Table 1.

TABLE 1

Comparison of dl5-29 yields of NCF treated or not treated with additives.

|  | Passage | Avg. Titer (pfu/mL) | Total pfu/NCF | pfu/cm$^2$ | pfu/cell |
|---|---|---|---|---|---|
| dl5-29 NCF with additives | 29 | 1.26E+07 | 1.26E+10 | 2.00E+06 | 12.63 |
| dl5-29 NCF without additives | 29 | 6.08E+06 | 6.08E+09 | 9.63E+05 | 6.08 |

Further analysis was performed to calculate the viral yield per cm$^2$, per NCF, and per cell. These calculations were based upon the total cm$^2$ of the NCF as 6320, and an estimation of a confluent NCF as having $1.0\times10^9$ total cells. In addition, passage numbers for the AV529-19 cells are shown at the time of infection. Results indicate a benefit from the sucrose and cholesterol additives. Pfu/cell data were consistent with, or slightly lower than previous studies, however, the passage number of the cells used was at the higher limit of optimum use.

Results from a pilot study utilizing 4 NCFs are shown on Table 2. The results show nearly $2.0\times10^{10}$ total pfu/NCF, with yield efficiencies of 18-19 pfu/cell. Yields were consistent throughout all four NCFs evaluated in this pilot study.

TABLE 2

Calculated average viral titers (pfu/mL), total pfu/NCF, pfu/cm², and pfu/cell of NCF viral harvests.

|  | Passage | Avg. Titer (pfu/mL) | Total pfu/NCF | pfu/cm² | pfu/cell |
|---|---|---|---|---|---|
| dl5-29 NCF 1 | 19 | 1.93E+07 | 1.93E+10 | 3.05E+06 | 19.29 |
| dl5-29 NCF 2 | 19 | 1.82E+07 | 1.82E+10 | 2.88E+06 | 18.21 |
| dl5-29 NCF 3 | 19 | 1.97E+07 | 1.97E+10 | 3.12E+06 | 19.71 |
| dl5-29 NCF 4 | 19 | 1.94E+07 | 1.94E+10 | 3.07E+06 | 19.38 |

Based on the results provided above, the best upstream yields obtained so far are about $1.9 \times 10^{10}$ pfu/NCF, corresponding to an average of 19 pfu/cell. This is more than a two-fold increase in viral yield as compared to previous runs without sucrose and cholesterol lipid concentrate. In the four-NCF pilot study, viral yields between NCFs were very consistent, ranging from 18 to 20 pfu/cell. The optimal conditions described here yield useful amounts of virus.

Additional studies were carried out using OptiPro, DMEM-F12, and Megavir media (see FIGS. 5A-8). Oneway analysis of the titer production by basal media type shows that Megavir and DMEM-F12 titers have a larger improvement on virus production with sucrose and cholesterol than OptiPro. This analysis also suggests that the titer improvement in OptiPro, under certain conditions, may not be statistically significant (FIGS. 5A-5C and FIG. 6).

Sucrose, as a single factor, has an impact on virus production, but cholesterol by itself does not improve the virus production (FIGS. 7A and 7B). The simultaneous presence of sucrose and cholesterol has a significant impact on virus production. To maximize the titer, the data suggest 1× cholesterol and 80 mM sucrose in DMEM-F 12 to be the optimal condition for viral production. Observed increases in viral production are partially due to an increase in the specific production rate of the cells, showing an increase in the presence of the sucrose and cholesterol from 57.9 PFU/cell to 85.3 PFU/cell (FIG. 8).

Methods
Design of the 4 NCF Pilot Study (Table 2)

The purpose of this study was to scale-up production of herpes simplex virus strain dl5-29 from infection of Vero (AV529-19) cells in four Nunc cell factories (NCFs; Nalge-Nunc). The cells can be grown in OptiPro SFM media (Invitrogen/GIBCO, catalog no. 12309-019) containing 10% fetal bovine serum (FBS; JRH, catalog no. 12106-500M), 4 mM L-glutamine (Invitrogen/GIBCO, catalog no. 25030-081), G418 (Invitrogen/GIBCO, catalog no. 10131-027), and supplemented with 50 mM sucrose (EMD, catalog no. SX1075-1) and 0.5× of a 250× cholesterol lipid concentrate (Invitrogen/GIBCO, catalog no. 12531-018). Infection media consisted of the same OptiPro media containing 1% FBS but lacking G418. Cell cultures were infected with an approximate MOI of 0.01, and allowed to incubate approximately 72 hours at 34° C. and 5% $CO_2$. Following incubation, NCFs were harvested. Aliquots were drawn for each unit for sonication and viral titer by standard plaque assay (described below), and bulk harvests were centrifuged and pelleted in stabilization buffer for downstream processing.

Preparation of 1 M Sucrose Concentrate in Optipro (400 mL)
Mix the following reagents and warm to 37° C.:
sucrose (136.92 g)
OptiPro SFM (200 mL)
FBS (10%; 40 mL)
L-glutamine (8 mL)
G418 (4 mL)
cholesterol lipid concentrate (0.8 mL)
When dissolved, QS volume to 400 mL total with OptiPro SFM, then filter sterilize (0.2 μm).

Preparation of Seeding Media for NCFs (Per L)
Mix the following reagents:
OptiPro SFM (868 mL)
FBS (10%; 100 mL)
L-glutamine (20 mL)
G418 (10 mL)
cholesterol lipid concentrate (2 mL)
When mixed well, remove 50 mL of media mixture and replace with 50 mL of 1 M sucrose concentrate in OptiPro SFM. The final mixture will have a sucrose concentration of 50 mM.

Preparation of 1 M Sucrose Concentrate in OptiPro (200 mL for Infection Media)
Mix the following reagents and warm to 37° C.:
sucrose (68.46 g)
OptiPro SFM (100 mL)
FBS (1%; 2 mL)
L-glutamine (4 mL)
cholesterol lipid concentrate (0.4 mL)
When dissolved, QS volume to 200 mL total with OptiPro SFM, then filter sterilize (0.2 μm).

Preparation of Infection Media for NCFs (Per L)
Mix the following reagents:
OptiPro SFM (968 mL)
FBS (1%; 10 mL)
L-glutamine (20 mL)
cholesterol lipid concentrate (2 mL)
When mixed well, remove 50 mL of media mixture and replace with 50 mL of 1 M sucrose concentrate in OptiPro. The final mixture will have a sucrose concentration of 50 mM.

Preparation of 10% Sucrose in 1× Stabilization Buffer
Mix the following reagents:
sucrose (10 g)
10× Stabilization Buffer (10 mL)
Add RODI to bring total volume to 100 mL. Mix well and then place in a 37° C. waterbath for approximately 30 minutes to fully dissolve. Filter-sterilize using a 0.2 μm sterile filter unit.

NUNC Cell Factory Seeding Procedure
Harvest 8 triple flasks of Vero cells (AV529-19) grown to approximately 90% confluence in OptiPro medium containing 10% FBS with 4 mM L-glutamine, and G418. Following harvest, draw off a 1 mL aliquot for cell count using a Vi-Cell instrument. Under aseptic conditions, seed NCFs at $10^8$ cells/NCF using pre-infection media (OptiPro SFM with 10% FBS+4 mM L-glutamine, G418, 50 mM sucrose and 0.5× cholesterol lipid mixture; 2 L). Grow to near confluence (approximately 3-4 days) in an incubator at 37° C. and 5% $CO_2$.

NUNC Cell Factory Infection Procedure
Pour off old media and rinse NCF with 500 mL DPBS and remove. Infect at full volume infection media (1 L) with dl5-29 at a MOI of 0.01 as follows, assuming $10^9$ cells per confluent NCF: NCF #1-4: $10^7$ pfu/NCF of HSV98 (dl5-29) in infection media (OptiPro SFM with 1% FBS+4 mM L-glutamine, 50 mM sucrose and 0.5× cholesterol lipid concentrate). Based on a stock titer of $1.6 \times 10^8$ pfu/mL, add 625 μL of virus stock per NCF. Incubate the NCFs at 34° C. for 72 hours or until approximately 100% CPE is evident.

NUNC Cell Factory Harvest Procedure
When 100% CPE (nearly 100% of cells rounded up and easily detached) is evident, tap NCFs several times to dislodge all cells from monolayer. With 100% CPE, cells should already be mostly detached. Aseptically pour off infection media from NCF into a sterile container. Mix well, then draw off 1 mL aliquot and add to sterile 15 mL centrifuge tube containing 3.75 mL of OptiPro SFM with 10% FBS and 4 mM L-glutamine, and 250 μL of HSA. This is used as a 1:5 dilution of the NCF harvest and is to be sonicated and titered to determine viral yield. Divide the NCF harvest equally into 4×250 mL sterile centrifuge tubes. Spin in centrifuge at 1000 RPM for 10 minutes at 4° C. Decant resulting supernatants and save in 1 L sterile bottle labeled as conditioned media. Store bottles at 4° C. Using 20 mL of 10% Sucrose in 1× Stabilization buffer, aseptically resuspend and combine pellets in BSC. Quick-freeze combined pellet and 1 mL centrifuge tube containing titer sample in ethanol/dry ice bath until frozen solid. Then place samples in −80° C. Freezer.

Sonication Procedure

Remove 15 mL centrifuge tubes containing titer samples and thaw quickly in a 37° C. waterbath. Immediately after thawing, place on ice. Aseptically sonicate cell suspension sample using probe sonicator; Outlet level 3, Duty cycle 40% for approximately 15 seconds/mL on ice (total of 75 seconds). Spin down sonicated suspension samples in centrifuge at 5000 g for 10 minutes at 4° C. to remove cell debris. Aseptically pour off supernatant into sterile, labeled 15 mL centrifuge tubes. Pellets are discarded and proceed directly to viral titer procedure.

Virus Infectivity Assay (Plaque A, Assay)

Test samples were tested in 12-well plates that were seeded with Vero cells ($4\times10^5$ cells/well) for virus infectivity and quantification. They were serially diluted 10-fold in duplicate in minimum essential medium (MEM) containing 1% FBS supplemented with 100 units/mL penicillin and 100 μg/mL streptomycin, and L-glutamine (completed cell culture medium). Dilutions were then plated onto the cells at 200 μL/well in triplicate wells. A positive control is also serially diluted and plated. The inoculated plates were incubated at 37° C. with 5% $CO_2$ for 60 minutes with rocking of the plates every 15 minutes to allow virus adsorption. One mL of completed medium with 0.8% methyl cellulose was added to each well and the plates were returned to incubation at 37° C. with 5% $CO_2$ for 2 days. Medium was then removed from all wells and approximately 1 mL of 1% crystal violet in 70% methanol was added to each well to fix and stain plates. Plates were left at room temperature for more than 60 minutes to stain cells, then the stain was removed, wells were washed with tap water, and the plates were air-dried. Viral plaques were counted using a stereomicroscope with plates held over a light box. Virus concentrations are expressed as pfu/mL. Further calculations are then made to determine the total viral yield per NCF, viral yield/$cm^2$, and viral yield/cell.

Other Embodiments

All references, publications, patent applications, and patents cited in this specification are herein incorporated by reference as if each individual publication or patent were specifically and individually indicated to be incorporated by reference. Use of singular forms herein, such as "a" and "the," does not exclude indication of the corresponding plural form, unless the context indicates to the contrary. Although the invention has been described in some detail by way of illustration and example for purposes of clarity of understanding, it will be readily apparent to those of ordinary skill in the art in light of the teachings of the invention that certain changes and modifications may be made thereto without departing from the spirit or scope of the appended claims.

Other embodiments are within the following claims.

What is claimed is:

1. A composition comprising (i) a growth medium supplemented with between 5 mM and 500 mM of a disaccharide and a lipid mixture, (ii) Vero cells that express herpes simplex virus 2 (HSV-2) polypeptides $U_L5$ and $U_L29$, and (iii) an HSV-2 having inactivating mutations in $U_L5$ and $U_L29$.

2. The composition of claim 1, wherein said disaccharide is sucrose, lactose, maltose, trehalose, or cellobiose, or a mixture thereof.

3. The composition of claim 1, wherein said disaccharide is present in said medium at 50 mM or 80 mM, or between 50 mM and 80 mM.

4. The composition of claim 1, wherein said medium further comprises methyl-β-cyclodextrin and/or serum.

5. The composition of claim 4, wherein said serum is fetal bovine serum (FBS).

6. The composition of claim 1, wherein said lipid mixture is from a plant, is synthetic, comprises cholesterol, and/or comprises stigmastanol.

7. The composition of claim 1, wherein said medium increases production of said HSV-2 in the cells by at least 10% relative to HSV-2 production in cells grown in a medium lacking said disaccharide and said lipid mixture.

8. A method of increasing herpesvirus production in cells, said method comprising culturing the composition of claim 1, wherein said composition increases production of the herpesvirus by at least 10% relative to a herpesvirus cultured in cells grown in a medium lacking said disaccharide or said lipid mixture, wherein said herpesvirus is a replication-defective herpesvirus having inactivating mutations in $U_L5$ and $U_L29$, optionally in combination with an inactivating mutation in $U_L41$.

9. The method of claim 8, wherein said cells are AV529-19 cells.

10. The method of claim 8, wherein said cells express the herpesvirus polypeptides $U_L5$ and/or $U_L29$.

11. The method of claim 8, wherein said disaccharide is sucrose, lactose, maltose, trehalose, or cellobiose, or a mixture thereof.

12. The method of claim 8, wherein said disaccharide is present at 50 mM or 80 mM, or between 50 mM and 80 mM.

13. The method of claim 8, wherein said medium further comprises methyl-β-cyclodextrin and/or serum.

14. The method of claim 13, wherein said serum is fetal bovine serum (FBS).

15. The method of claim 8, wherein said lipid mixture is from a plant, is synthetic, comprises cholesterol, and/or comprises stigmastanol.

16. The method of claim 8, wherein said method increases production of a herpesvirus in the cells by at least 10% relative to herpesvirus production in cells grown in a composition lacking said disaccharide and said lipid mixture.

17. The composition of claim 1, wherein said HSV-2 has an inactivating mutation in $U_L41$.

18. The composition of claim 1, wherein said HSV-2 is strain dl5-29.

19. The composition of claim 18, wherein said Vero cells are AV529-19 cells.

* * * * *